US009895087B2

(12) United States Patent
Lee et al.

(10) Patent No.: US 9,895,087 B2
(45) Date of Patent: Feb. 20, 2018

(54) WEARABLE APPARATUS FOR MEASURING POSITION AND ACTION OF ARM

(71) Applicant: ELECTRONICS AND TELECOMMUNICATIONS RESEARCH INSTITUTE, Daejeon (KR)

(72) Inventors: Hoo-Man Lee, Daejeon (KR); Joong-Bae Kim, Daejeon (KR); Young-Bong Bang, Seoul (KR); Chang-Hyuk Lee, Seoul (KR); Ji-Won Choi, Suwon-si (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 253 days.

(21) Appl. No.: 14/886,237

(22) Filed: Oct. 19, 2015

(65) Prior Publication Data

US 2017/0055883 A1   Mar. 2, 2017

(30) Foreign Application Priority Data

Aug. 25, 2015 (KR) .................. 10-2015-0119464

(51) Int. Cl.
| | | |
|---|---|---|
| *B25J 9/04* | (2006.01) | |
| *A61B 5/11* | (2006.01) | |
| *A61B 5/00* | (2006.01) | |
| *B25J 3/04* | (2006.01) | |
| *B25J 9/00* | (2006.01) | |
| *B25J 9/16* | (2006.01) | |
| *B25J 13/02* | (2006.01) | |
| *B25J 13/08* | (2006.01) | |

(52) U.S. Cl.
CPC .......... *A61B 5/1121* (2013.01); *A61B 5/6824* (2013.01); *B25J 3/04* (2013.01); *B25J 9/0006* (2013.01); *B25J 9/1689* (2013.01); *B25J 13/025* (2013.01); *B25J 13/085* (2013.01); *Y10S 901/15* (2013.01)

(58) Field of Classification Search
CPC ........................................ B25J 9/04
See application file for complete search history.

(56) References Cited

U.S. PATENT DOCUMENTS

| | | | | |
|---|---|---|---|---|
| 5,967,580 A | * | 10/1999 | Rosheim ............... | B25J 3/04 294/106 |
| 2008/0193260 A1 | * | 8/2008 | Yokokohji ............ | B25J 13/02 414/1 |
| 2012/0237319 A1 | * | 9/2012 | Jacobsen .............. | B25J 3/04 414/1 |

FOREIGN PATENT DOCUMENTS

| | | |
|---|---|---|
| KR | 10-2008-0114197 A | 12/2008 |
| KR | 10-2013-0106970 A | 10/2013 |

* cited by examiner

*Primary Examiner* — Robert R Raevis
(74) *Attorney, Agent, or Firm* — LRK Patent Law Firm

(57) ABSTRACT

A wearable apparatus for measuring position and action of an arm includes: a main frame worn on an upper body of a user; and an arm motion-measuring unit connected to a side of the main frame, having a plurality of joints, and worn on an arm of a user, in which at least any one of the joints of the arm motion-measuring unit has a straight-motional degree of freedom. Accordingly, an instructor can conveniently move both arms in the apparatus, can precisely instruct a two-arm robot in motions of the instructor's arms, can reduce learning time of the robot, and can make the robot quickly and accurately learn the motions.

17 Claims, 11 Drawing Sheets

WEARABLE APPARATUS FOR MEASURING POSITION AND ACTION OF ARM

CROSS REFERENCE TO RELATED APPLICATION(S)

This application claims the benefit of Korean Patent Application No. 10-2015-0119464, filed on Aug. 25, 2015, which is hereby incorporated by reference in its entirety into this application.

BACKGROUND OF THE INVENTION

1. Technical Field

The present invention relates to a wearable apparatus for measuring position and action of an arm. More particularly, the present invention relates to a wearable apparatus that is worn on a user's arm for measuring a position and action of the arm and enables a robot to intuitionally learn necessary actions by precisely and stably measuring movement of the arm.

2. Description of the Related Art

As robots are used in various fields, the robots increasingly replace people for work. Various types of robots are used to repeatedly perform relatively simple and easy work or to work under severe environments that are difficult for people to work in. Further, robots mimicking humans are now used in industrial fields to perform work that humans have conventionally performed, such as automated production processes or dangerous probes. Accordingly, there have been various attempts to enable a user to intuitionally control motions of robots so that the motions are similar to human motions.

The simplest method is to directly input the positions of joint spaces or work spaces of a robot through a computer language or a touching pendant. This method requires designing in advance motion tracks of a robot intended by a user, numerically calculating tracks corresponding to the motion tracks in a work space or a joint space, and then inputting the values into an input device. According to this method, it is possible relatively easily estimate simple motions in the process of designing tracks, but when motions are complicated, an accident such as a collision may be caused due to misjudgment of the user, and additionally the user must learn robot motions by trial and error.

There is another method that transmits a 3D position and rotation information to a robot, using a 3D controller such as a 6-axis force sensor on the front of a robot. This method is to enable a user to give a robot instruction to move by holding and operating the 3D controller by hand. According to this method, however, when a robot having over six degrees of freedom is controlled, the position of an end effector can be moved as it is intended, but the robot may take undesired postures due to a redundant degree of freedom. Further, since all of motions of the robot are learned only through movement of the front of the robot, intuition of implementing a robot is somewhat poor.

In order to teach a robot having a redundant degree of freedom to make desired postures and motions, it may be possible to attach a torque sensor to every joint instead of a 6-axis sensor and make the robot take desired postures by applying force to the body in addition to the front of the robot. However, even in this case, there is a need for making paths by keeping intermediate points and smoothly connecting them, and it takes long time to make the robot learn complicated motions.

When a person learns a motion, he/she simulates a motion of another person. It is preferable that a robot can also recognize and copy motions of the human, but equipment that has been developed thus far has difficulty in precisely recognizing human motions. Motion capture devices that are usually used for making animations are classified into a type that visually recognizes markers on a body, a type that corrects signals from an inertia sensor using software, and a type that requires wearing a mechanical device, but none of them can measure human motions with high precision. Those motion capture devices are sufficient for making the overall motion of the human such as is required for animation purposes, but there is a need for an arm motion capture device that is very precise and stable relative to the motion capture devices.

An exoskeletal wearable device may relatively precisely measure motions in comparison to other devices, but it is complicated, and especially the shoulders of the human have a complicated structure of 7-degree of freedom, but at present it is difficult to design a mechanism for measuring even only three-directional rotation. FIG. 1 shows a 3-degree of freedom link assembly rotating about the rotational center of a shoulder and FIG. 2 shows a link mechanism with an additional degree of freedom for the back in the 3-degree of freedom link assembly. These assemblies are designed such that their shoulder centers are supposed to be aligned to the shoulder center of a person, but the shoulder makes complicated motions, so it is difficult to keep the rotational centers of the assemblies aligned to the rotational center of the shoulder, and accordingly, it may be inconvenient to move the shoulder due to corresponding resistance. Further, it is difficult to design a device that precisely measures forearm pronation/supination.

SUMMARY OF THE INVENTION

Accordingly, the present invention has been made keeping in mind the above problems occurring in the prior art, and an object of the present invention is to provide a wearable apparatus for measuring position and action of an arm that is worn on a user's arm and enables a robot to intuitionally learn necessary actions by precisely and stably measuring movement of the arm.

In order to accomplish the above object, the present invention provides a wearable apparatus for measuring position and action of an arm which includes: a main frame worn on an upper body of a user; and an arm motion-measuring unit connected to a side of the main frame, having a plurality of joints, and worn on an arm of a user, in which at least any one of the joints of the arm motion-measuring unit has a degree of freedom for straight motion.

The joints may include: a shoulder joint connected to a side of the main frame; an upper arm member coupled to the shoulder joint; an elbow joint coupled to an end of the upper arm member; a lower arm member coupled to the elbow joint; and a wrist joint coupled to an end of the lower arm member, and at least any one of the shoulder joint, the upper arm member, the elbow joint, the lower arm member, and the wrist joint may have a degree of freedom for straight motion.

The shoulder joint may have a first degree of freedom for rotation, a second degree of freedom for rotation, and a third degree of freedom for rotation, the upper arm member may have a degree of freedom for straight motion, the elbow joint may have a fourth degree of freedom for rotation and a fifth degree of freedom for rotation, and the wrist joint may have a sixth degree of freedom for rotation, a seventh degree of freedom for rotation, and an eight degree of freedom for rotation.

Rotational axes of the first rotational degree of freedom and the second rotational degree of freedom, rotational axes of the second rotational degree of freedom and the third rotational degree of freedom, rotational axes of the fourth rotational degree of freedom and the fifth rotational degree of freedom, rotational axes of the sixth rotational degree of freedom and the seventh rotational degree of freedom, and rotational axes of the seventh rotational degree of freedom and the eighth rotational degree of freedom may be respectively perpendicular to each other.

The wrist joint may include a wrist support frame axially rotatably coupled to an end of the lower arm member, and a bearing including an inner race having a hole through which a user's wrist passes and an outer race rotatably holding and surrounding the inner race may be disposed between the lower arm member and the wrist support frame.

The wrist joint may include: a timing pulley connected to the inner race and rotatably disposed outside the outer race; an outer race timing belt wound around the timing pulley and surrounding the outer race; and a bearing encoder connected to a rotary shaft of the timing pulley.

A measuring sensor that measures and transmits movement of each of the joints to a main controller may be disposed on each of the joints.

The measuring sensor may be an absolute encoder or a potentiometer.

A straight-moving unit having the straight-motional degree of freedom may include: a first straight-moving frame; a second straight-moving frame having a first side to which the first straight-moving frame is longitudinally movably coupled; and a third straight-moving frame longitudinally movably coupled to a second side of the second straight-moving frame.

The straight-moving unit may have a movement distance measuring unit measuring movement distances of the second straight-moving frame and the first straight-moving frame.

The movement distance measuring unit may include: a first timing pulley rotatably disposed at a first side of the second straight-moving frame, and rolling on the first straight-moving frame when the second straight-moving frame is moved; a second timing pulley rotatably disposed at a second side of the second straight-moving frame, and rolling on the second straight-moving frame when the third straight-moving frame; a timing belt having both ends wound on the first timing pulley and the second timing pulley; and an encoder connected to a rotational shaft of the first timing pulley or a rotational shaft of the second timing pulley.

The movement distance measuring unit may measure a movement distance a straight-motional degree of freedom by measuring a rotational angle of any one of the first timing pulley and the second timing pulley or measuring an amount of movement of the first straight-moving frame or the second straight-moving frame.

The first straight-moving frame and the third straight-moving frame may be operated with the timing belt to move in opposite directions with respect to the second straight-moving frame.

The apparatus may further include: a lower frame mounted around the waist of a user; a first back support frame fixed to the lower frame; a second back frame fixed to the lower frame; and a back joint rotatably connecting the first back support frame and the second back support frame to each other.

The back joint may include: a back joint frame axially rotatably coupled to the second back frame; and a back joint bracket member coupled to the back joint frame rotatably to the left and right and coupled to the first back support frame rotatably up and down, thereby having a 3-degrees of freedom.

At least one of a gyroscope, an acceleration sensor, and a geomagnetic sensor may be mounted on the main frame to measure inclination or a torsional angle of the upper body of a user.

At least any one of the joints may have an actuator.

A force sensor may be disposed at an operation unit of a robot, and the joints may be operated or some of load generated when the joints are operated may be compensated, by a reactant force to a force sensed by the force sensor with the actuator.

According to the present invention, an instructor can conveniently move both arms in the apparatus, can precisely instruct a two-arm robot in motions of the instructor's arms, can reduce learning time of the robot, and can make the robot quickly and accurately learn the motions.

Therefore, according to the present invention, even a non-expert can conveniently and precisely instruct a robot even in complicated motions so that the robot can intuitionally learn the motions.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
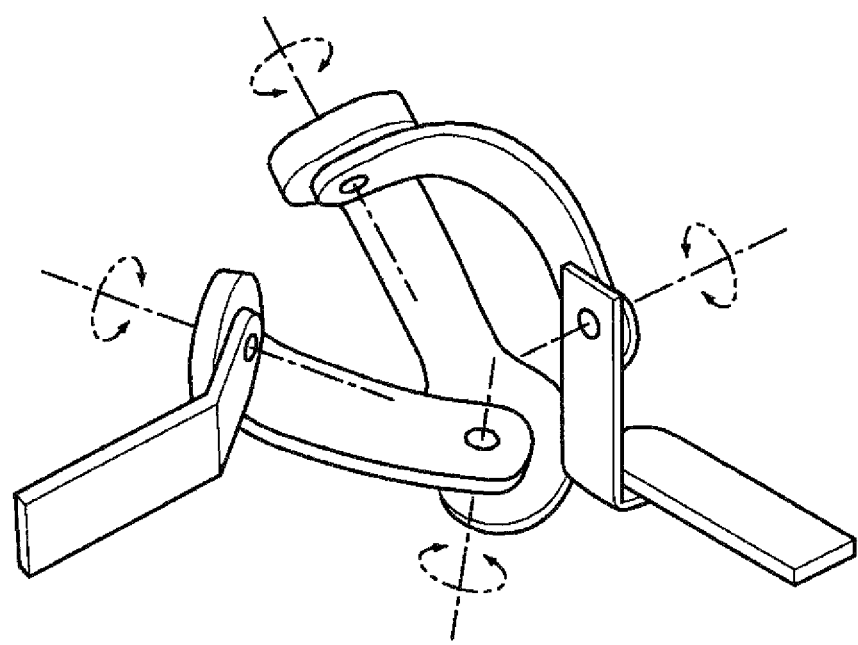
FIG. 1 is a schematic view showing a 3-degree of freedom link assembly of the related art.
Figure 2:
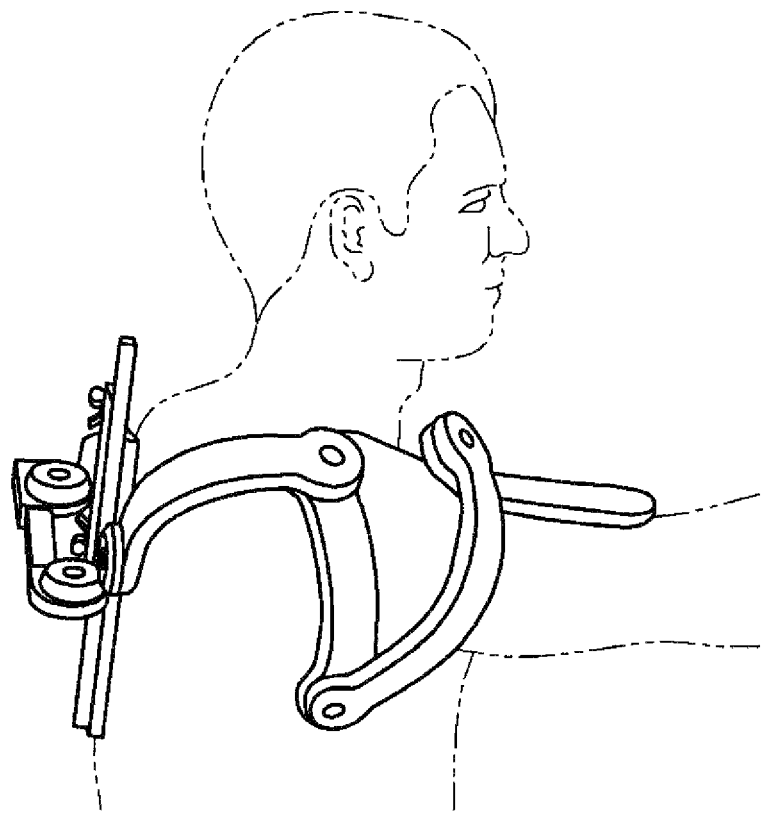
FIG. 2 is a schematic view showing a 3-degree of freedom link assembly worn by a user.

The present invention will be described in detail below with reference to the accompanying drawings. Repeated descriptions and descriptions of known functions and configurations which have been deemed to make the gist of the present invention unnecessarily obscure will be omitted below. The embodiments of the present invention are intended to fully describe the present invention to a person having ordinary knowledge in the art to which the present invention pertains. Accordingly, the shapes, sizes, etc. of components in the drawings may be exaggerated to make the description clearer.

Figure 3:
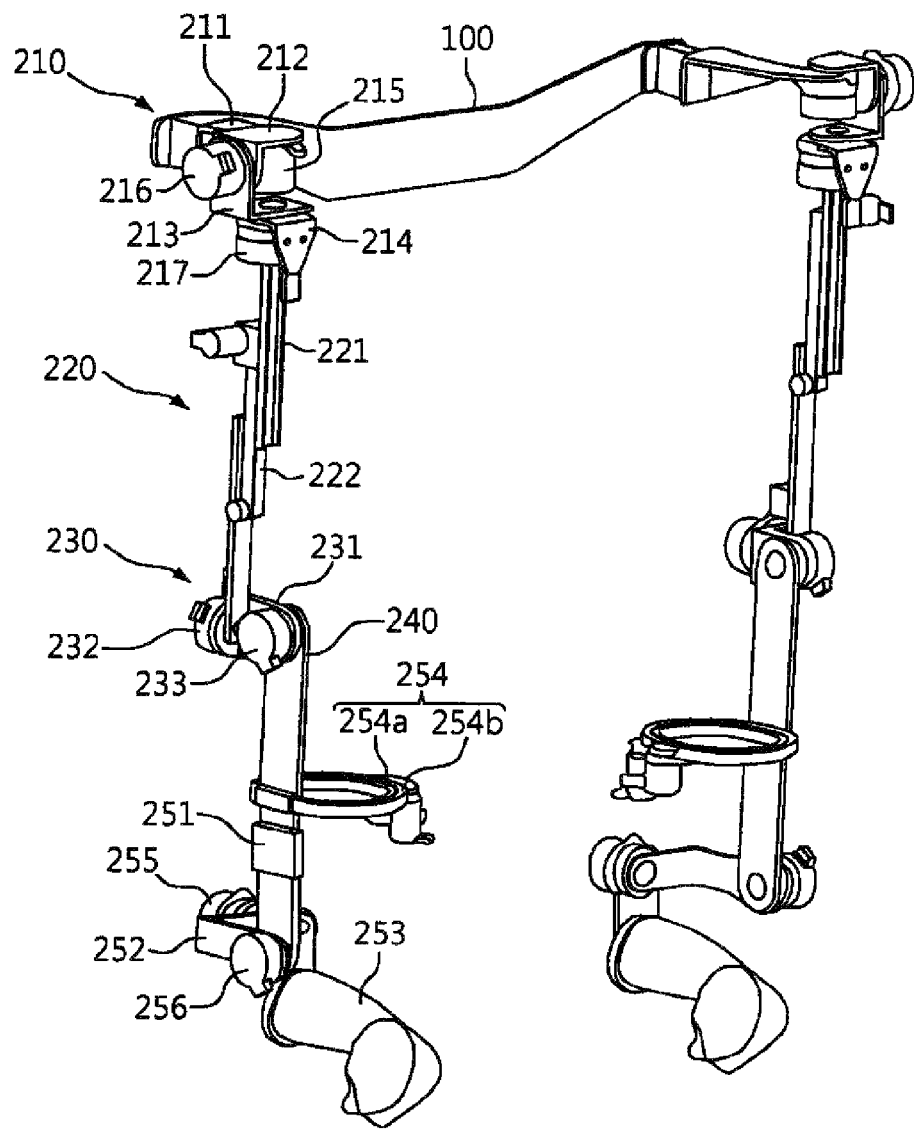
FIG. 3 is a perspective view showing an embodiment of a wearable apparatus for measuring position and action of an arm according to an embodiment of the present invention.
Figure 4:
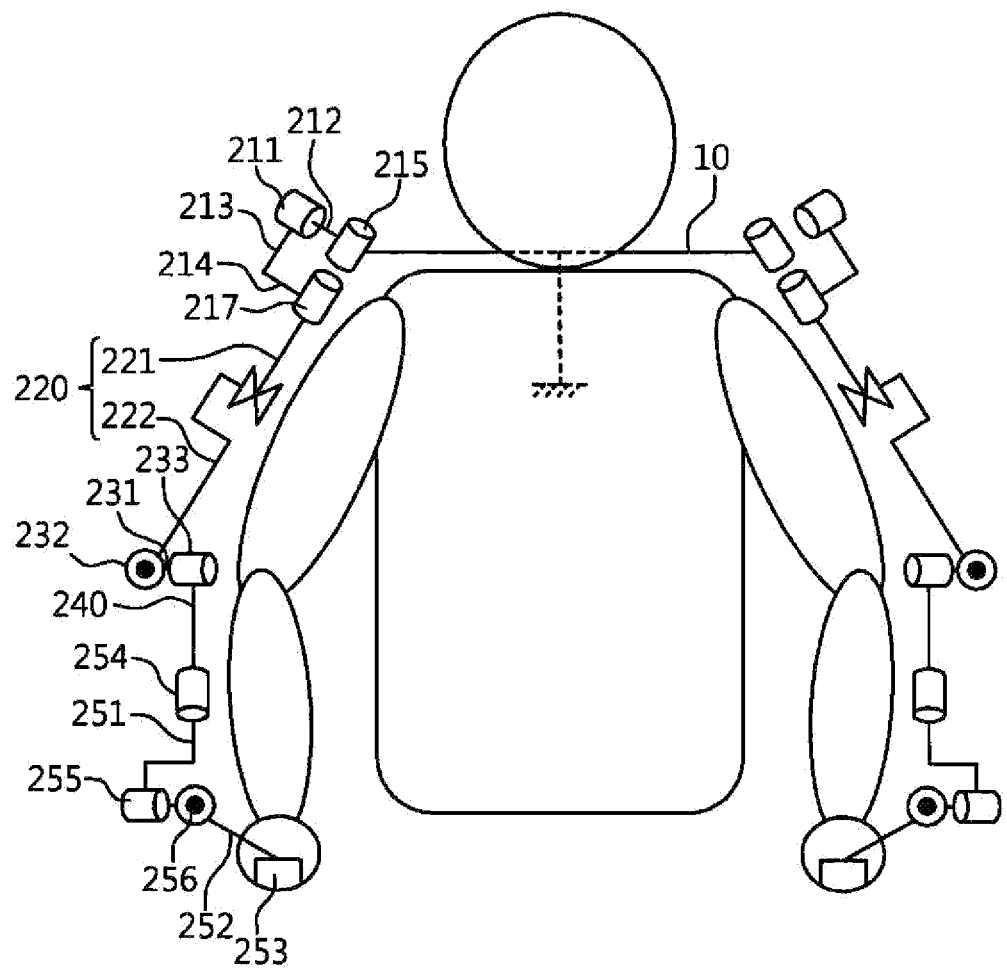
FIG. 4 is a schematic view showing an embodiment of a wearable apparatus for measuring position and action of an arm according to an embodiment of the present invention.

FIG. 3 is a perspective view showing an embodiment of a wearable apparatus for measuring position and action of an arm according to an embodiment of the present invention and FIG. 4 is a schematic view showing an embodiment of a wearable apparatus for measuring position and action of an arm according to an embodiment of the present invention.

A wearable apparatus for measuring position and action of an arm according to an embodiment of the present invention enables a user, that is, an instructor to wear a two-arm robot and precisely instruct the robot in desired motions from the instructor's arm motions by freely and conveniently moving both arms, and that enables a robot to intuitionally learn necessary motions.

Referring to FIGS. 3 and 4, a wearable apparatus for measuring position and action of an arm according to an embodiment of the present invention includes a main frame 100 that is put on the upper body of a user and arm motion-measuring units 200 that are connected to a side of the main frame 100, have a plurality of joints, and are put on arms of a user.

A straight-motional degree of freedom is given to at least any one of the joints of the arm motion-measuring units 200.

The arm motion-measuring units 200 are disposed at both sides of the main frame 100 and put on the arms of a user with the arm being freely movable, so the arm motion-measuring units 200 instruct the two-arm robot in the motion of the arms or make the two-arm robot learn the motion.

The arm motion-measuring unit 200 include a plurality of joints, which, for example, includes a shoulder joint 210 connected to a side of the main frame 100, an upper arm member 220 coupled to the shoulder joint 210, an elbow joint 230 disposed at an end of the upper arm member, a lower arm member 240 coupled to the elbow joint 230, and a wrist joint 250 disposed at an end of the lower arm member 240.

The arm motion-measuring unit 200 further includes a handle 253 coupled to the wrist joint 250, so when a user wears the robot, the shoulder joint 210 is spaced from a shoulder of the user with the handle 253 in a hand, and accordingly, rotation of the shoulder can be easily measured.

The shoulder joint 210, for example, includes: a first shoulder joint bracket member 211 protruding forward from a side of the main frame 100; a second shoulder joint bracket member 212 rotatably mounted on the first shoulder joint bracket member 211; a third shoulder joint bracket member 213 mounted on the second shoulder joint bracket member 212 rotatably in a direction different from the rotational direction of the second shoulder joint bracket member 212; and a fourth shoulder joint bracket member 214 mounted on the third shoulder joint bracket member 213 rotatably in a direction different from the rotational direction of the third shoulder joint bracket member 213, so 3-rotational degree of freedom is provided.

The second shoulder joint bracket member 212 enables a wearer to rotate an arm left and right, the third shoulder joint bracket member 213 enables a wearer to rotate an arm up and down, and the fourth shoulder joint bracket member 214 enables a wearer to axially rotate an arm.

The first shoulder joint bracket member 211, second shoulder joint bracket member 212, third shoulder joint bracket member 213, and fourth shoulder joint bracket member 214 are L-shaped brackets.

The second shoulder joint bracket member 212 is combined with the first shoulder joint bracket member 211 by a first shoulder hinge part 215 having a longitudinal rotational axis, so it can rotate left and right.

The third shoulder joint bracket member 213 is combined with the second shoulder joint bracket member 212 by a second shoulder hinge part 216 having a transverse rotational axis, so it can rotate up and down.

The fourth shoulder joint bracket member 214 is combined with the third shoulder joint bracket member 213 by a third shoulder hinge part 217 having a rotational axis in the longitudinal direction of an arm, so it can rotate left and right. The rotational axis of the fourth shoulder joint bracket member 214 may be disposed longitudinally or transversely at an angle, depending on the positions of the rotational axis of the second shoulder joint bracket member 212 and the rotational axis of the third shoulder joint bracket member 213.

The second shoulder joint bracket member 212, third shoulder joint bracket member 213, and fourth shoulder joint bracket member 214 can be rotated perpendicular to each other and may be freely modified as long as they make motions similar to actual motions of an arm of a wearer.

That is, the should joint 210 has a first rotational degree of freedom by the first shoulder hinge part 215, a second rotational degree of freedom by the second shoulder hinge part 216, and a third rotational degree of freedom by the third shoulder hinge part 217, and the rotational axes in the first rotational degree of freedom and the third rotational degree of freedom are perpendicular to the rotational axis in the second rotational degree of freedom therebetween.

The upper arm member 220 may include a first straight-moving frame 221 coupled to the shoulder joint 210 and a second straight-moving frame 222 coupled to the first straight-moving frame 221 and being longitudinally movable.

The first straight-moving frame 221 may be mounted on the fourth shoulder joint bracket member 214 and the elbow joint 230 may be coupled to an end of the second straight-moving frame 222.

The elbow joint 230 includes an elbow joint bracket member 231 rotatably coupled to an end of the upper arm member 220 and the lower arm member 240 can rotate in a direction different from the rotational direction of the elbow joint bracket member 231.

The elbow joint bracket member 231 is combined with the upper arm member 220, that is, the second straight-moving frame member 222 by a first elbow hinge part 232 having a rotational axis in the front-rear direction, so the upper arm member 220 can be rotated left and right or axially rotated.

The lower arm member 240 is coupled to the elbow joint bracket member 231 by a second elbow hinge part 233 having a transverse rotational axis, so it can rotate up and down.

In contrast, the elbow joint bracket member 231 may be made rotate up and down and the lower arm member 240 may be coupled to the elbow joint bracket member 231 such that it can rotate left and right or axially rotate.

That is, the elbow joint 230 has a fourth rotational degree of freedom by the first elbow hinge part 232 and a fifth rotational degree of freedom by the second elbow hinge part 233, and the rotational axes in the fourth rotational degree of freedom and the fifth rotational degree of freedom are perpendicular to each other and they may be freely modified as long as they make motions similar to actual motions of an arm of a wearer.

The wrist joint 250 is coupled to an end of the lower arm member 240 and includes a wrist support frame 251 rotatably coupled to an end of the lower arm member 240, a wrist joint bracket member 252 coupled to an end of the wrist support frame 251 rotatably in a direction different from the rotational direction of the wrist support frame 251, and a handle 253 coupled to the wrist joint bracket member 252 rotatably in a direction different from the rotational direction of the wrist joint bracket member 252, so it has 3-degree of freedom.

A bearing 254 including an inner race 254a having a hole through which a wrist of a user passes and an outer race 254b rotatably holding and surrounding the inner race 254a is disposed between the lower arm member 240 and the wrist support frame 261, the lower arm member 240 may be coupled to the outer race 254b of the bearing 254 and the wrist support frame 251 may be coupled to the inner race 254a of the bearing 254, so the wrist support frame 251 is axially rotatably coupled to an end of the lower arm member 240.

The wrist joint bracket member 252 is combined with the upper arm member 220, that is, the second straight-moving frame 222 by a first wrist hinge part 255 having a transverse rotational axis, so it can rotate up and down.

The handle 253 is coupled to the elbow joint bracket member 252 by a second wrist hinge part 256 having a transverse rotational axis, so it can rotate left and right.

The wrist support frame 251, the wrist joint bracket member 252, and the handle 253 can rotate in different directions, for example, perpendicular to each other, and they may be freely modified as long as they make motions similar to actual motions of a hand of a wearer.

That is, the wrist joint 250 has a sixth rotational degree of freedom by the bearing 254, a seventh rotational degree of freedom by the first wrist hinge part 255, and an eighth rotational degree of freedom by the second wrist hinge part 256, and the rotational axes in the seventh rotational degree of freedom and the eighth rotational degree of freedom are perpendicular to the rotational axis in the second rotational degree of freedom therebetween.

Figure 5:
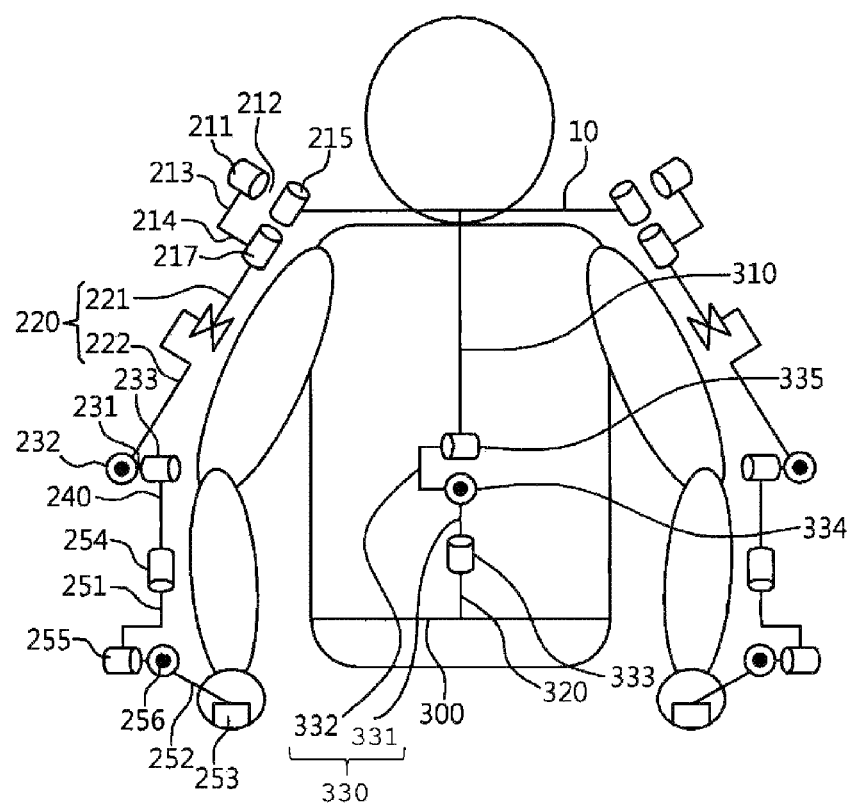
FIG. 5 is a schematic view showing another embodiment of a wearable apparatus for measuring position and action of an arm according to an embodiment of the present invention.

Referring to FIG. 5, the main frame 100 is mounted on the upper body of a user, close to a line transversely connecting both sides, that is, both shoulders. Another embodiment of a wearable apparatus for measuring position and action of an arm according to the present invention may farther include a lower frame 300 that is mounted around the waist of a user, a first back support frame 310 fixed to the lower frame 300, a second back frame 320 fixed to the lower frame 300, and a back joint 330 connecting the first back, support frame 310 and the second back support frame 320 such that they can rotate.

The back joint 330 may include a back joint frame 331 axially rotatably coupled to the second back frame 320, and a back joint bracket member 332 coupled to the back joint frame 331, rotatably to the left and right and coupled to the first back support frame 310, rotatably up and down, so it has 3-degrees of freedom.

The back joint frame 331 is combined with the second back joint frame member 320 by a first back hinge part 333 having a rotational axis disposed longitudinally, that is, in the longitudinal direction of the second back joint frame 320, so it can axially rotate.

The back joint bracket member 332 is combined with the back joint frame 331 by a second back hinge part 334 having a rotational axis disposed in the front-rear direction, so it can rotate left and right.

The back joint bracket member 332 is coupled to the first back support frame 310, rotatably up and down by a third back hinge part 335 having a transverse rotational direction.

That is, the should joint 210 has a first degree of freedom for back rotation for rotation by the first back hinge part 333, a second degree of freedom for back rotation for rotation by the second back hinge part 334, and a third degree of freedom for back rotation for rotation by the third back hinge part 335, and the rotational axes in the first degree of freedom for back rotation for rotation, the second degree of back-rotational direction, and the third degree of freedom for back rotation for rotation are perpendicular to each other.

The back joint 330 can measure movement of even the upper body of a user, that is, an instructor so the robot can learn the movement.

At least one of a gyroscope, an acceleration sensor, and a geomagnetic sensor 110 is mounted on the main frame 100 to additionally measure inclination or a torsional angle of the upper body of a user.

Figure 6:
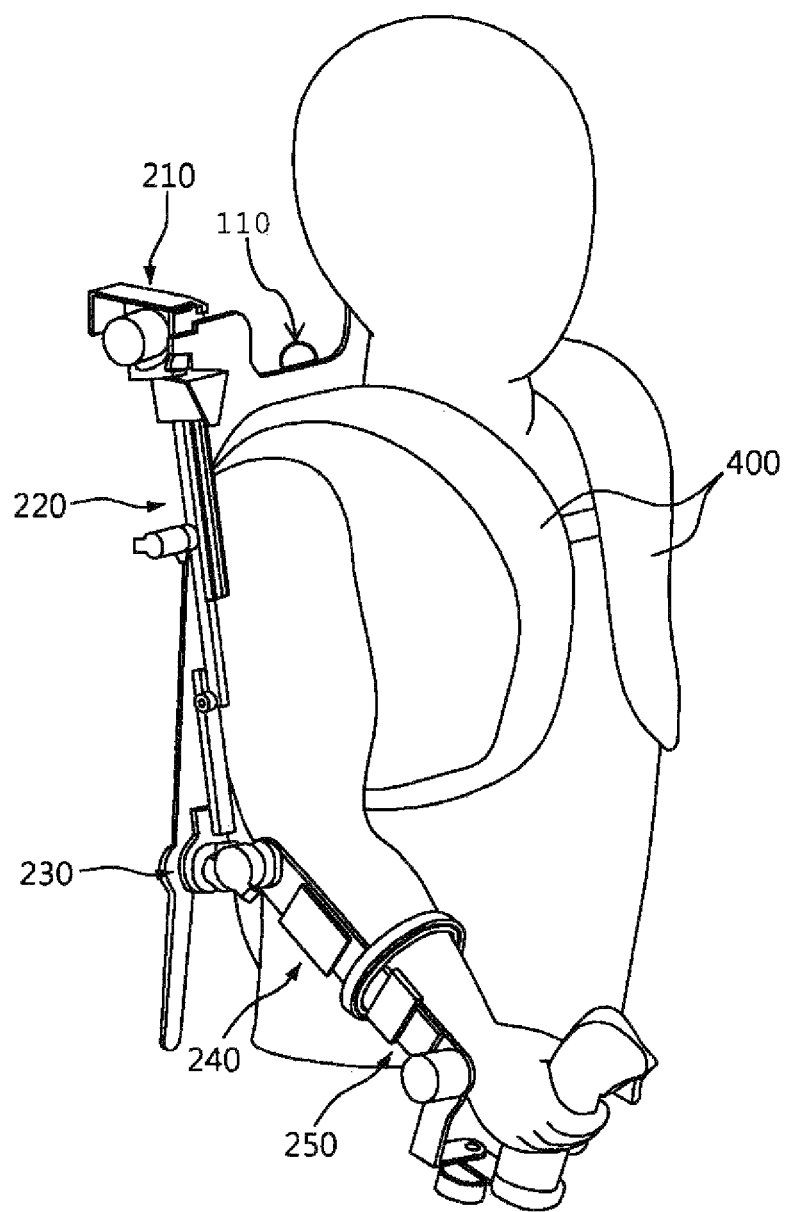
FIG. 6 is a perspective view showing an example of wearing a wearable apparatus for measuring position and action of an arm according to an embodiment of the present invention.

Referring to FIG. 6, a wearable apparatus for measuring position and action of an arm according to the present invention further include wearing members 400 for wearing the main frame 100 on the upper body of a user.

The wearing members 400 may be shoulder bands that can be carried on both shoulders of a user and may be modified in any type known in the art as long as they can allow the main frame 100 to be carried on the upper portion of the back of a user.

When a user wears the wearable apparatus for measuring position and action of an arm, the shoulder joints are spaced from the shoulders of the user so that rotation of the shoulders can be easily measured, the upper arm members 200 and the lower arm members 240 are positioned to correspond to the upper arms and the lower arms of the user, and the user freely move both arms with the handle 253 in hands so that a two-arm robot can learn the movement of both arms.

Though not shown, the wearable apparatus for measuring position and action of an arm of the present invention has a measuring sensor at each joint that measures and transmits movement of the joints to a main controller, so when a user freely moves both arms in the apparatus, the measuring sensors transmit movement measured at the joints is to the main controller, and the main controller can keep the movement of the arm motion-measuring units 200 transmitted from the measuring sensors to control movement of a two-arm robot later, can instruct the two-arm robot in movement by transmitting movement the same as the movement transmitted from the measuring sensor to the two-arm robot, and can keep the movement in an operation controller of the two-arm robot for instructing.

The measuring sensors may be absolute encoders or potentiometer.

That is, the first shoulder hinge part 215, second shoulder hinge part 216, third shoulder hinge part 217, first elbow hinge part 232, second elbow hinge part 233, first wrist hinge part 255, second wrist hinge part 256, first back hinge part 333, second back hinge part 334, and third back hinge part 335 are each equipped with a measuring sensor that measures a rotational range and values measured by the measuring sensors are transmitted to the main controller.

Figure 7:
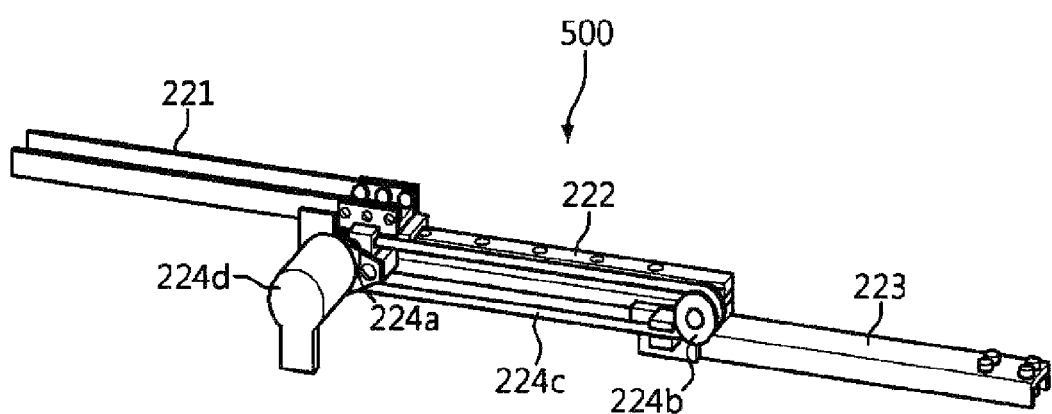
FIGS. 7 and 8 are views showing an example of a straight-motional degree of freedom in a wearable apparatus for measuring position and action of an arm according to the present invention.
Figure 8:
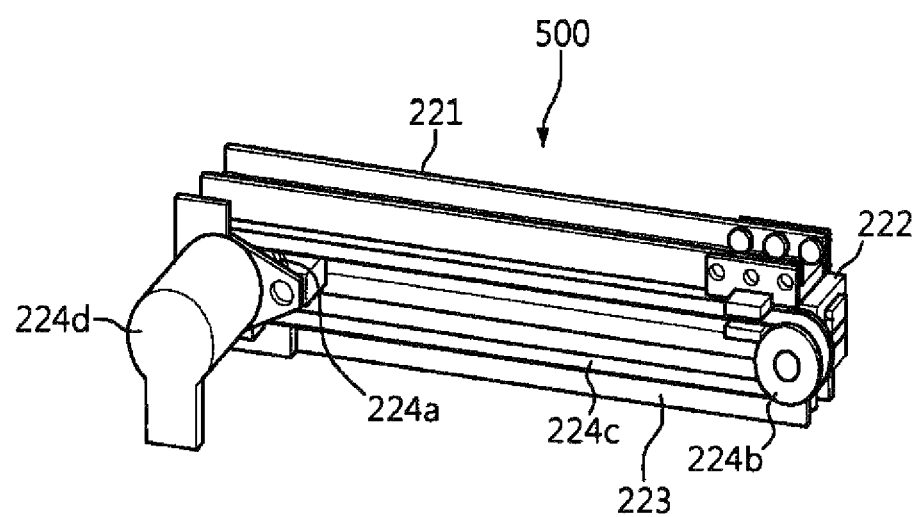

FIGS. 7 and 8 are views showing an example of a straight-motional degree of freedom in a wearable apparatus for measuring position and action of an arm according to the present invention. Referring to FIGS. 7 and 8, a straight-moving unit 500 having a straight-motional degree of freedom may include a first straight-moving frame 221, a second straight-moving frame 222 with a first end to which the first straight-moving frame 221 longitudinally movably coupled, and a third straight-moving frame 223 longitudinally coupled to a second end of the second straight-moving frame 222.

The straight-moving units may have a movement distance-measuring unit that measures movement distances of the second straight-moving frame 222 and the first straight-moving frame 221. The movement distance-measuring units are connected to the main controller and transmit measured information to the main controller, and the main controller can instruct the two-arm robot in movement on the basis of the information transmitted from the movement distance measuring units and can keep movement in the operation controller of the two-arm robot for instructing.

The movement distance-measuring unit includes a first timing pulley 224a that is rotatably disposed at one side of the second straight-moving frame 222 and rolls on the first straight-moving frame 221 when the second straight-moving member 222 is moved, a second timing pulley 224b that is rotatably disposed at a second side of the second straight-moving frame 222 and rolls on the second straight-moving frame 222 when the third straight-moving 223 is moved, a timing belt 224c of which both ends are wound around the first timing pulley 224a and the second timing pulley 224b, and an encoder 224d connected to a rotational shaft of the first timing pulley 224a or a rotational shaft of the second timing pulley 224b.

The movement distance-measuring unit can measure a straight movement distance with a straight-motional degree of freedom by measuring the rotational angle of any one of the first timing pulley 224a and the second timing pulley 224b or measuring the amount of movement of the first straight-moving frame 221 or the second straight-moving frame 222.

The first straight-moving frame 221 and the third straight-moving frame 223 are operated with the timing belt 224c such that they move in opposite directions with respect to the second straight-moving frame 222, so a long stroke can be achieved in comparison to the contraction length.

Figure 9:
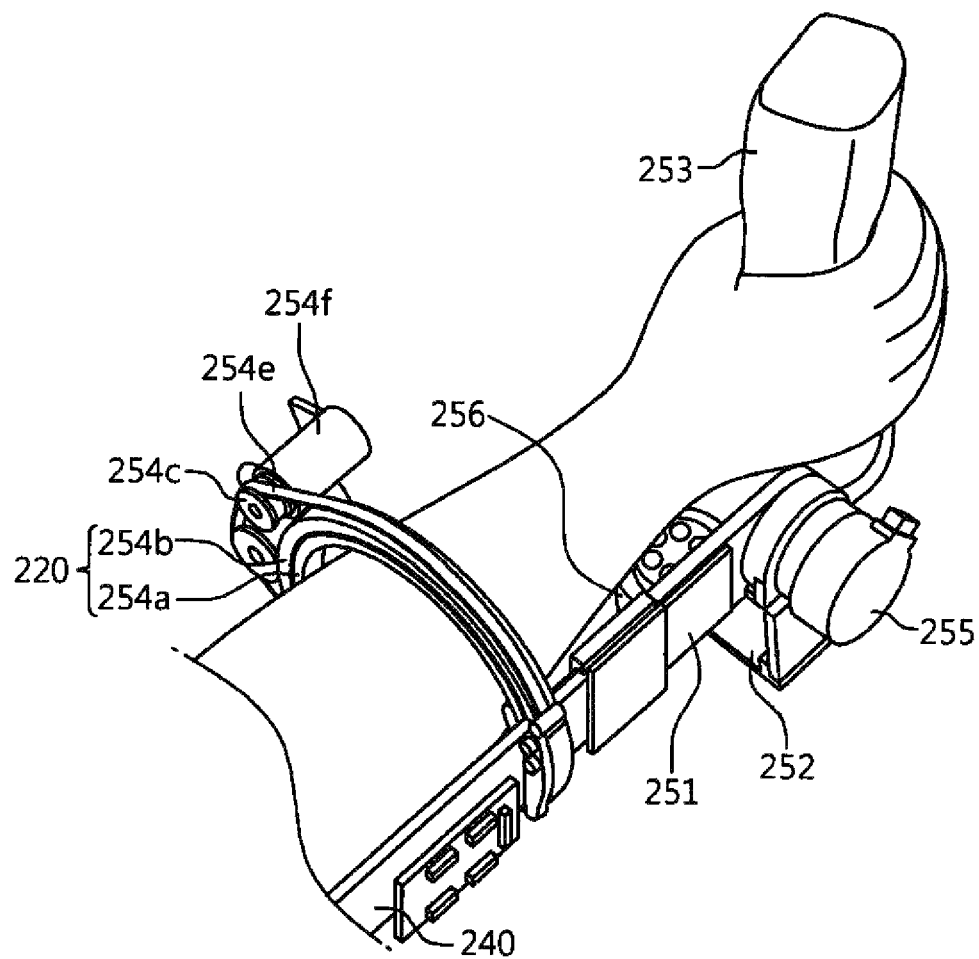
FIGS. 9 and 10 are perspective views showing an example of a wrist joint in a wearable apparatus for measuring position and action of an arm according to the present invention.
Figure 10:
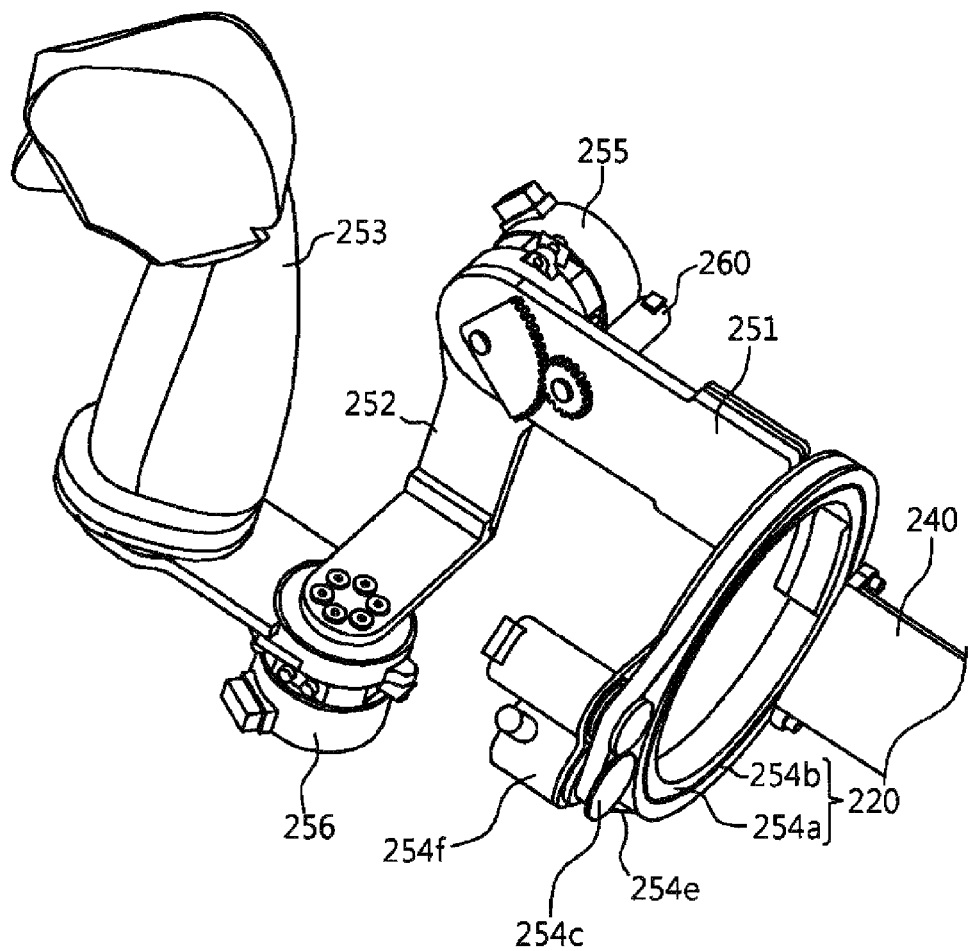

FIGS. 9 and 10 are perspective views showing an example of the wrist joint 250 in a wearable apparatus for measuring position and action of an arm according to the present invention. Referring to FIG. 9, the lower arm member 240 is coupled to the outer race 254b of the bearing 254 and the wrist support frame 251 is coupled to the inner race 254a of the bearing 254, so the wrist support frame 251 can be axially rotated.

The wrist joint 250 may include a timing pulley 254c connected to the inner race 254a, disposed outside the outer race 254b, and being rotatable, an outer race-timing belt 254e wound around the timing pulley 254c and surrounding the outer face 254b, and a bearing encoder 254f connected to a rotational shaft of the timing pulley 254c.

When a user rotates a wrist with the handle 253 in a hand, the inner race 254a is rotated, the timing pulley 254c is rotated by the outer race-timing belt 254e, and the bearing encoder 254f senses the rotation and measures the rotational range of the inner race 254a, that is, the axial rotational range of the user's wrist.

Referring to FIG. 10, any one of the joints may have an actuator 260.

FIG. 10 shows an example in which the actuator 260 is integrally mounted on the first wrist hinge part 255, and though not shown, the actuator 260 may be mounted on at least any one of other joints, that is, the first shoulder hinge part 215, second shoulder hinge part 216, third shoulder hinge part 217, first elbow hinge part 232, second elbow hinge part 233, second wrist hinge part 256, first back hinge part 333, second back hinge part 334, and the third back hinge part 335 to operate the joints.

The wearable apparatus for measuring position and action of an arm according to the present invention can be very useful as a master device for instructing a two-arm robot in motions in an industrial field or remotely controlling a two-arm robot used in dangerous area, in a nuclear power station, or in space/under water.

It is possible to enable a user, that is, an instructor to feel a force applied to a slave robot that follows movement of the wearable apparatus for measuring position and action of an arm according to the present invention, by installing a force sensor at an operation unit of the slave robot, installing the actuator 260 at each of main joints of the arm motion-measuring units 200, and operating the joints with a reactant force to the force sensed by the force sensors, using the actuators 260.

Further, when a user wears the wearable apparatus for measuring position and action of an arm according to the present invention for a long time, the user can smoothly move by compensating for some of load that is generated when the joints are operated, by operating the actuators 260 at the joints.

Figure 11:
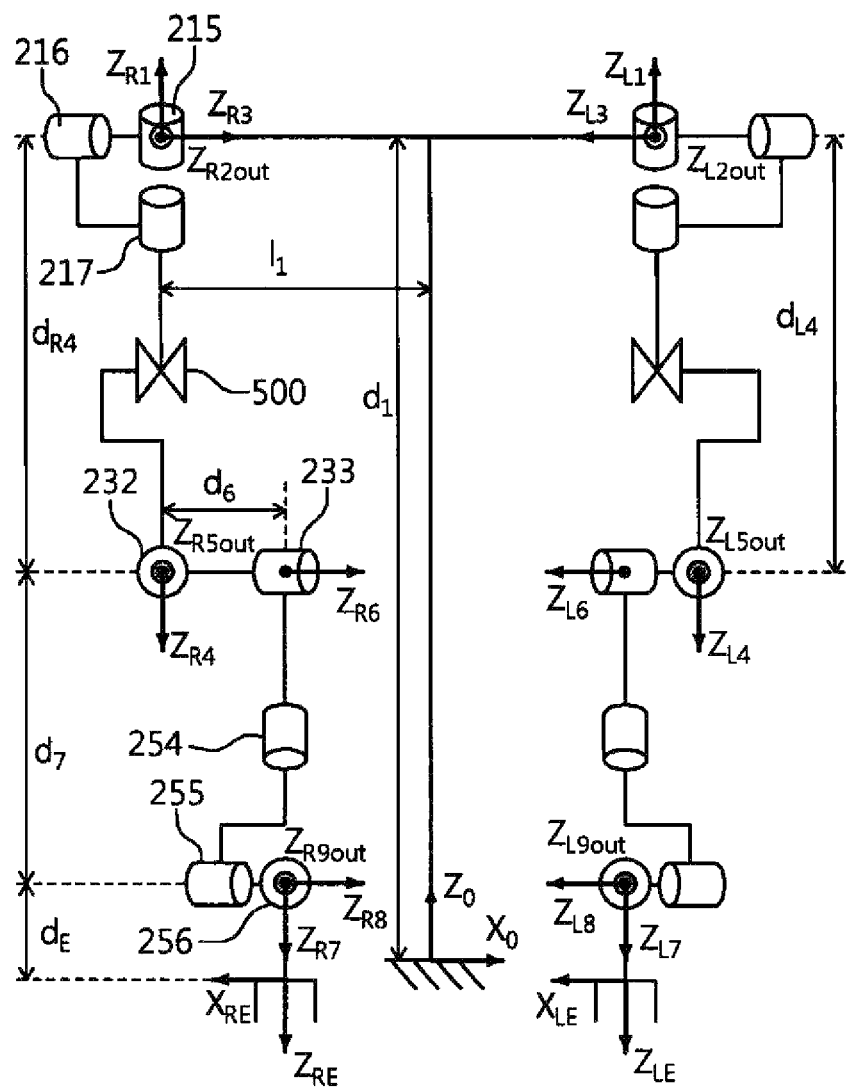
FIG. 11 is a view showing DH parameters for mechanical calculation by a wearable apparatus for measuring position and action of an arm according to the present invention.

FIG. 11 is a view showing DH parameters for mechanical calculation by the wearable apparatus for measuring position and action of an arm according to the present invention. DH parameters in a degree of freedom of the joints are shown in the following Table 1, in which the rotational axes of adjacent joints are perpendicular to each other.

TABLE 1

|  | $\alpha_{i-1}$ | $a_{i-1}$ | $d_i$ | $\theta_i$ |
|---|---|---|---|---|
| $Z_{R1}/Z_{L1}$ | 0 | $-1_1$ | $d_1$ | $\theta_{R1} - \pi/2$ |
| $Z_{R2}/Z_{L2}$ | $-\pi/2$ | 0 | 0 | $\theta_{R2}$ |
| $Z_{R3}/Z_{L3}$ | $\pi/2$ | 0 | 0 | $\theta_{R3} + \pi/2$ |
| $Z_{R4}/ZL_4$ | $\pi$ | 0 | $d_{R4}$ | 0 |
| $Z_{R5}/Z_{L5}$ | $-\pi/2$ | 0 | 0 | $\theta_{R5} - \pi/2$ |
| $Z_{R6}/Z_{L6}$ | $-\pi/2$ | 0 | $d_6$ | $\theta_{R6} - \pi/2$ |
| $Z_{R7}/ZL_7$ | $-\pi/2$ | 0 | $d_7$ | $\theta_{R7}$ |
| $Z_{R8}/Z_{L8}$ | $\pi/2$ | 0 | 0 | $\theta_{R3} + \pi/2$ |
| $Z_{R9}/Z_{L9}$ | $\pi/2$ | 0 | 0 | $\theta_{R6} - \pi/2$ |
| $Z_{RE}/Z_{LE}$ | $-\pi/2$ | 0 | $d_E$ | 0 |

According to the present invention, an instructor can conveniently move both arms in the apparatus, can precisely instruct a two-arm robot in motions of the instructor's arms, can reduce learning time of the robot, and can make the robot quickly and accurately learn the motions.

Therefore, according to the present invention, even a non-expert can conveniently and precisely instruct a robot even in complicated motions so that the robot can intuitionally learn the motions.

As described above, optimal embodiments of the present invention have been disclosed in the drawings and the specification. Although specific terms have been used in the present specification, these are merely intended to describe the present invention and are not intended to limit the meanings thereof or the scope of the present invention described in the accompanying claims. Therefore, those skilled in the art will appreciate that various modifications and other equivalent embodiments are possible from the embodiments. Therefore, the technical scope of the present invention should be defined by the technical spirit of the claims.

What is claimed is:

1. A wearable apparatus for measuring position and action of an arm, comprising:
 a main frame worn on an upper body of a user; and
 an arm motion-measuring unit connected to a side of the main frame, having a plurality of joints and a plurality of arm members, and worn on an arm of a user,
 wherein at least one of the plurality of arm members of the arm motion-measuring unit has a straight-motional degree of freedom, and
 wherein a straight-moving unit having the plurality of arm members includes:
 a first straight-moving frame;
 a second straight-moving frame having a first side to which the first straight-moving frame is longitudinally movably coupled; and
 a third straight-moving frame longitudinally movably coupled to a second side of the second straight-moving frame.

2. The apparatus of claim 1,
 wherein the plurality of joints include:
 a shoulder joint connected to a side of the main frame;
 an elbow joint coupled to an end of the upper arm member; and
 a wrist joint coupled to an end of the lower arm member,
 wherein the plurality of arm members include:
 an upper arm member coupled to the shoulder joint; and
 a lower arm member coupled to the elbow joint; and
 wherein at least one of the upper arm member and the lower arm member has a straight-motional degree of freedom.

3. The apparatus of claim 2, wherein:
 the shoulder joint has a first rotational degree of freedom, a second rotational degree of freedom, and a third rotational degree of freedom,
 the upper arm member has a straight-motional degree of freedom,
 the elbow joint has a fourth rotational degree of freedom and a fifth rotational degree of freedom, and
 the wrist joint has a sixth rotational degree of freedom, a seventh rotational degree of freedom, and an eighth rotational degree of freedom.

4. The apparatus of claim 3, wherein rotational axes of the first rotational degree of freedom and the second rotational degree of freedom, rotational axes of the second rotational degree of freedom and the third rotational degree of freedom, rotational axes of the fourth rotational degree of freedom and the fifth rotational degree of freedom, rotational axes of the sixth rotational degree of freedom and the seventh rotational degree of freedom, and rotational axes of the seventh rotational degree of freedom and the eighth rotational degree of freedom are respectively perpendicular to each other.

5. The apparatus of claim 2, wherein:
 the wrist joint includes a wrist support frame axially rotatably coupled to an end of the lower arm member, and
 a bearing including an inner race having a hole through which a user's wrist passes and an outer race rotatably holding and surrounding the inner race is disposed between the lower arm member and the wrist support frame.

6. The apparatus of claim 5, wherein the wrist joint includes:
 a timing pulley connected to the inner race and rotatably disposed outside the outer race;
 an outer race timing belt wound around the timing pulley and surrounding the outer race; and
 a bearing encoder connected to a rotary shaft of the timing pulley.

7. The apparatus of claim 1, wherein a measuring sensor that measures and transmits movement of each of the joints to a main controller is disposed on each of the joints.

8. The apparatus of claim 7, wherein the measuring sensor is an absolute encoder or a potentiometer.

9. The apparatus of claim 1, wherein the straight-moving unit further includes a movement distance measuring unit for measuring movement distances of the second straight-moving frame and the first straight-moving frame.

10. The apparatus of claim 9, wherein the movement distance measuring unit includes:
 a first timing pulley rotatably disposed at a first side of the second straight-moving frame, and rolling on the first straight-moving frame when the second straight-moving frame is moved;
 a second timing pulley rotatably disposed at a second side of the second straight-moving frame, and rolling on the second straight-moving frame when the third straight-moving frame;
 a timing belt having both ends wound on the first timing pulley and the second timing pulley; and
 an encoder connected to a rotational shaft of the first timing pulley or a rotational shaft of the second timing pulley.

11. The apparatus of claim 10, wherein the movement distance measuring unit measures a movement distance of a straight-motional degree of freedom by measuring a rotational angle of one of the first timing pulley and the second timing pulley or measuring an amount of movement of the first straight-moving frame or the second straight-moving frame.

12. The apparatus of claim 10, wherein the first straight-moving frame and the third straight-moving frame are operated with the timing belt to move in opposite directions with respect to the second straight-moving frame.

13. The apparatus of claim 1, further comprising:
 a lower frame mounted around a waist of a user;
 a first back support frame fixed to the lower frame;
 a second back frame fixed to the lower frame; and
 a back joint rotatably connecting the first back support frame and the second back support frame to each other.

14. The apparatus of claim 13, wherein the back joint includes:
 a back joint frame axially rotatably coupled to the second back frame; and
 a back joint bracket member coupled to the back joint frame rotatably to the left and right and coupled to the first back support frame rotatably up and down, thereby having a 3-degree of freedom.

15. The apparatus of claim 1, wherein at least one of a gyroscope, an acceleration sensor, and a geomagnetic sensor is mounted on the main frame to measure inclination or a torsional angle of the upper body of a user.

16. The apparatus of claim 1, wherein at least one of the joints has an actuator.

17. The apparatus of claim 16,
 wherein a force sensor is disposed at an operation unit of a robot, and wherein the joints are operated or a part of load generated when the joints are operated is compensated with the actuator, by a reactant force to a force sensed by the force sensor.

* * * * *